United States Patent [19]

Martin et al.

[11] Patent Number: 5,527,823
[45] Date of Patent: *Jun. 18, 1996

[54] PESTICIDAL FORMULATIONS

[75] Inventors: Robert Martin; David A. Jeffries; Denise K. North; John M. Groome, all of Berkhamsted; Peter L. Crampton; Andrew J. Huson, both of Hertfordshire, all of United Kingdom

[73] Assignee: Roussel UCLAF, France

[*] Notice: The term of this patent shall not extend beyond the expiration date of Pat. No. 5,466,458.

[21] Appl. No.: 193,701

[22] Filed: Feb. 8, 1994

Related U.S. Application Data

[63] Continuation-in-part of Ser. No. 924,044, Aug. 24, 1992, abandoned, and a continuation-in-part of Ser. No. 979,452, Nov. 22, 1992, abandoned, which is a continuation of Ser. No. 845,804, Mar. 9, 1992, abandoned, which is a continuation of Ser. No. 438,399, Dec. 27, 1989, abandoned.

[30] Foreign Application Priority Data

Mar. 2, 1988 [GB] United Kingdom ............ 8804988
Aug. 20, 1990 [GB] United Kingdom ............ 9018227

[51] Int. Cl.$^6$ ............ A01N 37/34; A01N 57/08; A01N 53/08; A01N 25/22
[52] U.S. Cl. ............ 514/521; 514/89; 514/531; 514/122; 514/637; 514/549; 514/367; 514/594; 514/119; 504/706; 71/DIG. 1; 424/405
[58] Field of Search ............ 514/89, 521, 531, 514/122, 637, 549, 367, 594, 119; 504/206; 71/DIG. 1; 424/405

[56] References Cited

U.S. PATENT DOCUMENTS

| 4,320,139 | 3/1992 | Takei et al. ............ 424/282 |
| 4,351,754 | 9/1982 | Dupre ............ 524/445 |
| 5,037,653 | 8/1991 | Dawson ............ 424/405 |

FOREIGN PATENT DOCUMENTS

| 0331474 | 6/1989 | European Pat. Off. |
| 2095109 | 9/1982 | United Kingdom. |
| 8807326 | 10/1988 | United Kingdom. |

Primary Examiner—Richard L. Raymond
Assistant Examiner—Deborah Lambkin
Attorney, Agent, or Firm—Bierman & Muserlian

[57] ABSTRACT

A formulation suitable for spraying or for dilution with water to form a sprayable preparation, the formulation comprising an active ingredient, optionally a carrier or solvent for the active ingredient, an emulsifier and an evaporation retardant, characterized in that the formulation satisfies formula $$\frac{\text{mass of oil phase}}{\text{mass of retardant}} \leq \frac{M_{oil}}{M_{retardant}} \times \text{Exp}\left[\frac{\ln\left(\frac{L}{4}\right) + C\ln(AX^B)}{C}\right] \quad (I)$$

where L is less than or equal to 15, A=700376, B=−1.51, C=0.8472, $M_{oil}$ is the weighted average relative molar mass of the oil phase $M_{retardant}$ is the weighted average relative molar mass of the retardant, and X=($M_{oil}$) 1.8/Y, where Y is the molar solubility ration of the formulation, defined as the minimum number of moles of the oil phase which will dissolve the retardant, divided by the number of moles of retardant, provided that, in the formula above, any solvent which has no liquid phase at 27° C. at atmospheric pressure is excluded. The formulation may comprise a pesticide or herbicide. The action of the evaporation retardant is improved.

18 Claims, No Drawings

PESTICIDAL FORMULATIONS

PRIOR APPLICATIONS

This application is a continuation-in-part of U.S. patent application Ser. No. 924,044, filed Aug. 24, 1992, now abandoned and of U.S. patent application Ser. No. 979,452, filed Nov. 22, 1992, which is a continuation of U.S. patent application Ser. No. 845,804, filed Mar. 9, 1992, which is a continuation of U.S. patent application Ser. No. 438,399 filed Dec. 27, 1989 all abandoned.

SPRAY FORMULATIONS

The present invention relates to spray formulations, especially pesticidal formulations of the sort which may be diluted with water to form a sprayable preparation, for example a pressure pack ("aerosol") preparation or a spray, particularly an ultra low volume (ULV) spray for domestic, horticultural, agricultural, environmental or industrial use.

Water-based sprays are advantageous because they cost less than oil-based sprays and are often less toxic to mammals. However, particularly when the ambient temperature is high, the water in the spray droplets evaporates and the droplets become smaller and drift more readily from the area being sprayed. The size of the droplets is frequently specially chosen to suit the application, for example to maximize droplet adherence to flying insects or adherence to plant Foliage, to increase bio-availability, or to control the size of the area being sprayed and the delivery rate per square meter; such care is pointless if the spray droplets change size, possibly unpredictably, following spraying.

GB-A-2 095 109 discloses improved water-dilutable formulations comprising a long-chain fatty alkanol which retards the evaporation of the water from the drops of the spray.

We have now found that still better evaporation retardation can be achieved if the Formulation satisfies the following Formula:

$$\frac{\text{mass of oil phase}}{\text{mass of retardant}} \leqq \frac{M_{oil}}{M_{retardant}} \times \mathrm{Exp}\left[\frac{\ln\left(\frac{L}{4}\right) + C\ln(AX^{B})}{C}\right]$$

where L is less than or equal to 15, A=700376, B=−1.5, C=0.8472

$M_{oil}$ is the weighted average relative molar mass of the oil phase $M_{retardant}$ is the average molar mass of the retardant, and $$X = \frac{(M_{oil})^{1.8}}{Y}$$

where Y is the molar solubility ratio of the formulation, defined as the minimum number of moles of oil phase which will dissolve the retardant, divided by the number of moles of retardant, provided that, in the Formula above, any solvent which has no liquid phase at 27° C. at atmospheric pressure is excluded.

For the avoidance of doubt, and to clarify any ambiguities which may arise in the printing or copying of this specification, it is to be noted that the relational symbol in the Formula is "less than or equal to" , "Exp" means the exponential of what follows in brackets, "in" means the natural logarithm, i.e. $\log_e$, L is divided by 4 , X is raised to the power B, B is a negative value (minus 1.51) and, in the definition of X, $M_{oil}$ is raised to the power 1.8.

The "oil phase" is the liquid non-aqueous phase and will comprise one or more of the active ingredient, the solvent therefor and the emulsifier.

Preferably L, which is related to the evaporation rate from the sprayed droplets, is less than 12, 10, or 8 and is most preferably less than 5. A distilled water spray has an "L" value of about 26, and most conventional diluted formulations have a value of about 22–30. In the formulations of the invention, "L" can be set at a desired value in order to calculate the required ratios of the ingredients. "L" can also be measured for a given formulation by the method described below.

The evaporation retardant may be any film-forming compound, preferably an alkanol. It is preferably a primary alcohol: preferably with no more than one or two side substitutions selected from methyl, ethyl, trifluoromethyl and halo (e.g. fluoro or chloro), with such substitutions preferably remote from the alcohol group (preferably at least 7 carbon atoms away from the hydroxyl group), and preferably the alkanol is not substituted at all: preferably $C_{16-20}$; preferably saturated: and preferably a solid at 27° Octadecan-1-ol and, particularly, hexadecan-1-ol are preferred. Hexadecan-1-ol (also known as cetyl alcohol) is usually available commercially as a mixture with a minor proportion of octadecan-1-ol (stearyl alcohol) and such "cetostearyl alcohol" is quite satisfactory. Heptadecan-1-ol performs adequately but is much more expensive. Other highly effective film-forming agents include 1-hexadecylamine, 1-heptadecylamine and 1-octadecylamine. Less preferred film-forming agents include hexadecan-2-ol, 1,2-hexadecandiol, methyl stearate, stearyl acetate, methyl palmirate and 1,2-octadecandiol. N-alkoxyalkanols may be used, for example $CH_3(CH_2)_{21}OC_2H_4OH$, $CH_3(CH_2)_{21}OC_3H_6OH$, $CH_3(CH_2)_{17}OC_2H_4OH$ or $CH_3(CH_2)_{15}OC_2H_4OH$, as may oxyethylene-docosanol and mixtures of any of the said evaporation retardants.

The emulsifier may be any suitable compound or mixture of compounds. Cationic emulsifiers can be used, but they tend to irritate the users' eyes. Anionic emulsifiers such as calcium dodecyl benzene sulphate (CDBS) or sodium di-isopropyl naphthalene sulphonate (SDNS) can also be used, but these are not as effective at stabilizing the emulsion. Preferably, the emulsifier is a non-ionic compound, or mixture of non-ionic compounds, having an HLB (hydrophilic/lipophilic balance) of 8–18. Suitable compounds include polyoxyethylene stearyl ethers(PSE), polyoxyethylene monolaurates(PEM), polyoxyethylene mono-oleates (PMO), sorbitan mono-oleate (SMO), nonylphenol ethoxylate (NPE), polyethylene glycol (PEG) and blends of oleyl ethoxylate (10 mole) and PEG20 glyceryl oleate (OE/PGO).

These emulsifiers are available as follows:

| Abbrev | Trade name | Supplier |
|---|---|---|
| OE/PGO | Tegoplant EM11 | Th. Goldschmidt Ltd |
| PSE | Brij 72, Brij 76, Brij 78 | ICI Speciality Chemicals |
| PEM | Tween 20 | ICI Speciality Chemicals |
| SMO | Span 80 | ICI Speciality Chemicals |
| PMO | Tween 80 | ICI Speciality Chemicals |

-continued

| Abbrev | Trade name | Supplier |
| --- | --- | --- |
| NPE | Ethylan KEO, 55, BV | Lankro Chemicals Limited |
| CDBS | Arylan CA | Lankro Chemicals Limited |
| SDN | Aerosol OS | Cyanamid GB Ltd |

The solvent, at least for an oil-soluble active ingredient, preferably has a low relative molecular mass, namely less than about 200. Suitable compounds include lower alkyl esters, lower ketones, lower alkanols and lower alkanes, the term "lower" meaning $C_{1-10}$, preferably $C_{1-5}$.

Particular solvents include the following, all available from Exxon Chemicals Limited. "Solvesso 150"—An aromatic hydrocarbon solvent (C9 to C11) with a distillation range 190° to 210° C. "Solvesso 200"—An aromatic hydrocarbon solvent (C10 to C12) with a distillation range 226° to 290° C. "Exxate 700"—Heptyl acetate 99% pure, or odorless kerosene—A mixture of high boiling non-aromatic hydrocarbons consisting of paraffins and naphthenes with a distillation range of 180° to 270° C.

The formulation may comprise more than one active ingredient (optionally with a synergist or potentiator, which is regarded as an active ingredient for the purpose of the Formula above, more than one solvent, more than one emulsifier and/or more than one retardant, together with other ingredients such as perfumes, dyes, anti-foam agents, solids especially to form wettable powders) and thickeners. Some compounds, such as butane, propane and dichlorodifluoromethane and carbon dioxide are highly volatile and are used as propellants in pressure pack formations. Although sometimes acting as solvents for particular active ingredient, they almost instantly evaporate from the drops when sprayed and are thus excluded from the calculations in the Formula above. Such solvent/propellants are those which have no liquid phase at 27° C. at atmospheric pressure.

In a modification of the formulations of the invention, particularly pesticidal formulations which contain two incompatible pesticides, are useful. It has been found that an anhydrous formulation of a pesticide, i.e. one which does not contain an aqueous phase, may be formulated with a second immiscible phase which contains a second pesticide. This has the advantage that incompatible pesticides may be incorporated in the same formulation.

Accordingly to this modification, the invention provides a two-phase formulation, the first phase of which comprises a first active ingredient, a stabilizer, and optionally an emulsifier or wetting or dispersing agent, and a carrier or solvent for the active ingredient; and a second phase immiscible with the first phase which comprises a second active ingredient and optionally an emulsifier or wetting or dispersing agent and a carrier or solvent for the second active ingredient.

Normally, the first active ingredient is dissolved or dispersed into the first phase but when the active ingredient is a liquid, a solvent is not always required. The second phase which is immiscible with the first phase contains the second active ingredient either dissolved or dispersed in the second phase. Preferably, the first phase is a water immiscible phase and the second phase is a water phase.

The first and second active ingredients are preferably physically and/or chemically incompatible when contained in a single phase, i.e. the presence of one of the actives in a formulation normally affects adversely the stability or utility of the other active. In addition, the active ingredient in the first phase may be one which has properties, for example irritancy or noxious vapor, which may be avoided by formulating it according to the present invention. Thus, it may have been possible previously to prepare stable but irritant formulations of the active ingredients; formulations of the invention may avoid such irritancy.

By active ingredient we mean both non-biologically and biologically active compounds. For example, the active ingredients may be selected from insecticides, acaricides, herbicides, fungicides, insect and plant growth regulators, pheromones, insect behavior modifiers, biological control agents (e.g. viruses, bacteria and eggs of parasites), dyes, perfumes, flavors, bactericides, lubricants, medicaments, food supplements, paints, polishes, lacquers (including hair lacquer), textile treatments (including sizes), or other active ingredients which are limited in their use by their incompatibility with other active ingredients. Examples of incompatible actives include combinations of pesticides selected from arthropodicides (insecticides, acaricides), herbicides, fungicides or insect and plant growth regulators. Examples of incompatible pesticides are the pyrethroids and organophosphate insecticides, the pyrethroid and formamidine insecticides, α-cyano-pyrethroid insecticides and thiazole anthelmintics, and pyrethroids and tributyl tin fungicides. Examples of incompatible pesticides are the pyrethroids and organophosphate insecticides, the pyrethroid and formamidine insecticides, α-cyano-pyrethroid insecticides and thiazole anthelmintics, and pyrethroids and tributyl tin fungicides.

Examples of pyrethroid insecticides include those of the formula (I)

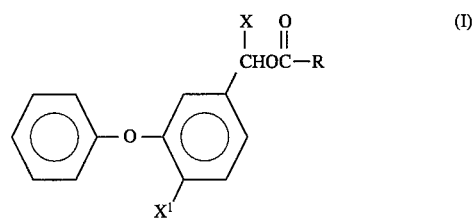

where R is

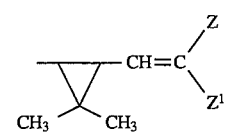

or

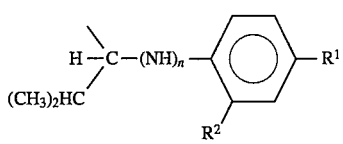

and n is 0 or 1, $R^1$ is halo $CF_3$ or $CHF_2O$, $R^2$ is hydrogen or halo, and Z and $Z^1$ are each independently selected from halo, $CF_3$ and methyl, X is hydrogen or halo, and X is H, CN or C≡CH

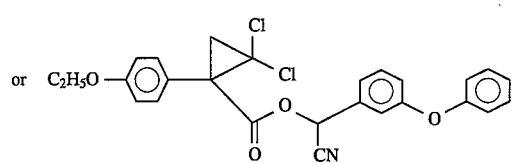

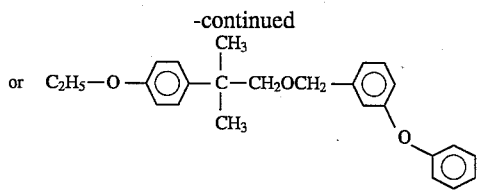

Examples of pyrethroids are 3-phenoxybenzyl-(1RS)-cis, trans-3-(2,2-dichlorovinyl)- 2,2-di-methyl-cyclopropane-1-carboxylate (permethrin), (RS)-α-cyano-3-phenoxybenzyl-(1RS)-cis,trans-3-(2,2-dichlorovinyl)- 2,2-dimethylcyclopropane-1-carboxylate (cypermethrin) and its individual isomers such as the (1RS) cis isomer (alphamethrin), (S)-α-cyano-3-phenoxybenzyl-(1R)-cis-3-(2,2-dibromovinyl)-2,2-dimethyl cyclopropane-1-carboxylate (deltamethrin), or a reaction mixture comprising two enantiomeric pairs in approximately ratio 2:3 (S)-α-cyano-3-phenoxybenzyl-(1R)-cis-3-(2,2-dichlorovinyl)-2,2-dimethylcyclopropanecarboxylate and (R)-α-cyano-3-phenoxybenzyl (1S)-cis-3-(2,2-dichlorovinyl)-2,2-dimethylcyclopropanecarboxylate with (S)-α-=cyano-3-phenoxybenzyl (1R)-trans-3-(2,2-dichlorovinyl)-2,2-dimethylcyclopropanecarboxylate and (R)-α-cyano-3-phenoxybenzyl(1S)-trans-3-(2,2-dichlorovinyl)-2,2-dimethylcyclopropanecarboxylate (beta-cypermethrin), (RS)-α-cyano-3-phenoxybenzyl-(Z)-(1RS)-cis-3-(2-chloro-3,3,3-trifluoro propenyl)-2,2-dimethylcyclopropanecarboxylate (cyhalothrin) and a mixture of its (S)(Z)-(1R)-cis and (R)(Z)-(1S)-cis-isomers; (RS)-α-cyano-3-phenoxybenzyl (RS)-2-(4-chlorophenyl)-3-methylbutyrate (fenvalerate) and the single (S), (S) isomer (esfenvalerate) (RS)-α-cyano-3-phenoxybenzyl (S)-2-(4-difluoromethoxyphenyl)-3-methyl butyrate (flucythinate), (RS)-α-cyano-3-phenoxybenzyl N(2-chloro-α, α,α -trifluoro-p-tolyl)-D-valinate(fluvalinate), (RS)-α-cyano-4-fluoro- 3-phenoxybenzyl(1RS)-cis-trans-3-(2,2-dichlorovinyl)-2,2-dimethylcyclopropanecarboxy late (cyfluthrin), (RS)-α-cyano-4-fluoro-3-phenoxybenzyl (1RS)-cis-trans-3-(2-chloro-2(4-chlorophenyl)vinyl)-2,,2-dimethylcyclopropanecarboxylate (flumethrin), 2-methylbiphenyl-3-yl-methyl(Z)-(1RS,3RS)-3RS)-3-(2-chloro-3,3,3-trifluoroprop-1-enyl)2,2-dimethylcyclopropane carboxylate (Bifenthrin); the allethrins, for example (1RS)-3-allyl-2-methyl-4-oxocylopent-2-enyl (1R, 3R)-2,2-dimethyl-3-(2-methylprop-1-enyl)cyclopropanecarboxylate (bioallethrin), (1S)-allyl-2-methyl-4-oxocyclo-pent-2-enyl (1R, 3R)-2,2-dimethyl-3-(2-methylprop-1-enyl)cyclopropanecarboxylate (S-bi-oallethrin), and mixtures of allethrin isomers (esbiothrin); the resmethrins, for example 5-benzyl-3-furylmethyl(1RS, 3RS; 1RS, 3SR)-2,2-dimethyl-3-(2-methyl-prop-1-enyl)cyclopropanecarboxylate (resmethrin) and 5-benzyl-3-furylmethyl (1R,3R)-2,2-dimethyl-3-(2-methylprop-1-enyl)cyclopropanecarboxylate (bioresmethrin).

Examples of organophosphate insecticides are:
0,0-dimethyl-0-3,5,6-trichloro-2-pyridylphosphorothioate (Chloropyri-fos-methyl)

Examples of formamidine insecticides include N-methyl bis(2,4-xylylaminomethyl)amine (Amitraz). Examples of thiazole anthelmintics include 2,3,5,6-tetrahydro-6-phenylimidazo[2,1-b]thiazole(levamisole).

Examples of fungicides include tributyl tin oxide.

Particularly preferred examples of incompatible actives in the formulations of the present invention include deltamethrin and chlorpyrifos methyl in an aqueous system.

The first phase is preferably dispersed within the second phase. The stabilizer forms a barrier at the interface between the dispersed first phase and the second phase. The stabilizer is preferably a film-forming alkanol e.g. an alkanol which can act as an evaporation retardant in an aqueous spray system as described in European Patent Specification 331474. It is preferably a primary alcohol; preferably with no more than one or two side substitutions selected from methyl, ethyl, trifluoromethyl and halo (e.g. fluoro or chloro), with such substitutions preferably remote from the alcohol group (preferably at least 7 carbon atoms away from the hydroxyl group), and preferably the alkanol is not substituted at all; preferably $C_{16-20}$; preferably saturated; and preferably a solid at 27° C., Octadecan-1-ol and, particularly, hexadecan-1-ol are preferred. Hexadecan-1-ol (also known as cetyl alcohol) is usually available commercially as a mixture with a minor proportion of octadecan-1-ol (stearyl alcohol) and such "cetostearyl alcohol" is quite satisfactory. Heptadecan-1-ol performs adequately but is much more expensive. Other highly effective film-forming agents include 1-hexadecylamine, 1-heptadecylamine and 1-octadecylamine. Less preferred film-forming agents include hexadecan-2-ol, 1,2-hexadecandiol, methyl stearate, stearyl acetate, methyl palmirate and 1,2-octadecandiol. N-alkoxyalkanols may be used, for example $CH_3(CH_2)_{21}OC_2H_4OH$, $CH_3(CH_2)_{21}OC_3H_6OH$, $CH_3(CH_2)_{CH17}OC_2H_4OH$ or $CH_3(CH_2)_{15}OC_2H_4OH$, as may oxyethylene-docosanol and mixtures of any of the said film-forming compounds.

The first phase may comprise more than one active ingredient (optionally with a synergist or potentiator, which is regarded as an active ingredient for the purpose of the Formula below), more than one solvent, more than one emulsifier and/or more than one stabilizer, together with other ingredients such as perfumes and dyes. $M_{oil}$, the average molecular weight of the oil phase, is the weight average, i.e. taking into account the relative proportions of the ingredients.

The value "Y", namely the molar solubility ratio of the formulation, may be derived empirically by making up at 40° C. a series of mixtures with different ratios of oil phase to alkanol, allowing the mixtures to cool to 27° C., leaving the cool mixtures for at least 48 hours at 27° C., and determining the amount, in moles, of the oil phase which is needed to dissolve completely a given amount of retardant, in moles. The former is then divided by the latter to give Y.

The formulations of the invention may be (i) single phase substantially anhydrous formulations, or (ii) emulsions comprising water. In a formulation of type (ii), some of the active ingredient, solvent or emulsifier components may partition into the aqueous phase, in which case such components are deemed not to be part of the oil phase in the Formula above. Examples of water-miscible solvents include ethanol, propanol, ethylene glycol and propylene glycol. It has been found that partially water-miscible components may be treated as being wholly water-miscible and hence excluded from the oil phase in the calculations.

When the formulation of the invention is diluted to give a sprayable preparation, the molar ratio of water to retardant should preferably not exceed about 9000, and preferably not exceed 8000, 7000 or 6000. It is perfectly possible to prepare a more dilute solution, but all that will happen is that the retardant will be unable to form a film over the entire surface of the droplets, and the water will evaporate until there is a sufficient concentration of the retardant to form a complete film which will then retard further evaporation. Thus, the droplet size is less controllable and, in addition, a larger volume of solution must be stored and pumped, which is inefficient.

The active ingredient of the one phase compositions may be an insecticide, acaricide, herbicide, fungicide, plant growth regulator, insect behavior modifier, biological control agent (e.g. viruses, bacteria and eggs of parasites), dye, perfume, bactericide, lubricant, medicament, paint, polish, lacquer (including hair lacquer), textile treatment (including sizes), or any other compound to be sprayed in a water-based formulation. Sprays in accordance with the invention are particularly suitable for spraying buildings, residential or commercial areas and insect breeding grounds (such as stamps and other tracts of water) with insecticide and for spraying crops with herbicides, insecticides, fungicides and plant growth regulators.

Suitable pesticides including pyrethroids (such as permethrin, deltamethrin, cypermethrin (including alphamethrin, the allethrins, fenvalerate and cyfluthrin), organophosphates (such as ethion, chlorfenvinphos, chlorpyrifos (methyl) or coumaphos), carbamates, organochlorines (such as DDT, dieldrin, dicofol, chlorpropylate or tetradifon), lipid amides, bicyclooctanes and dithianes. Suitable herbicides include glyphosate.

The sprays may be delivered by pumping through a nozzle, especially a sonic nozzle, by pumping over an ultrasonic nebulizer, or via a spinning disc. The droplets may be electro-statically charged, if desired.

As well as the uses discussed above, at least some of the formulations of the invention can be used to form a larvicidal Film over a lake.

To determine whether a given formulation satisfies the Formula given above, the following procedure may be adopted. If the formulation is an emulsion, the emulsion should first be "broken" by extraction of the concentrate with a suitable solvent such as ether. The ingredients are then analyzed by suitable quantitative and qualitative analytical methods. If not already known, the miscibility of each component with water is tested: if the component is water-miscible in the conditions of the Formulation, it is excluded From the calculations. The solubility of the evaporation retardant in the oil phase (excluding water-miscible components) is determined. The parameters are then operated on in the manner defined in the Formula to see whether the (mass of oil phase)/(mass of retardant) ratio is less than or equal to the figure on the right hand side of the Formula. This procedure is explained below with specific reference to the Examples.

In a preferred aspect, the first phase of the two phase formulation satisfies the formula:

$$\frac{\text{mass of oil phase}}{\text{mass of stabiliser}} \leqq \frac{M_{oil}}{M_{stabiliser}} \times \text{Exp}\left[\frac{\ln(L/4) + C\ln(AX^B)}{C}\right]$$

where L is less than or equal to 15, A=700376, B=−1.51, C=0.8472 $M_{oil}$ is the weighted average relative molar mass of the oil phase $M_{stabilizer}$ is the average molar mass of the stabilizer, and $$X = \frac{(M_{oil})^{1.8}}{Y}$$

where Y is the molar solubility ratio of the formulation, defined as the minimum number of moles of oil phase which will dissolve the stabilizer, divided by the number of moles of stabilizer, provided that, in the Formula above, any solvent which has no liquid phase at 27° C. at atmospheric pressure is excluded.

The "oil phase" is the liquid non aqueous phase and will comprise one or more of the active ingredient, the solvent therefor and in some cases the emulsifier.

Preferably L is less than 12, 10, or 8 and is most preferably less than 5. A distilled water spray has an "L" value of about 26, and most conventional diluted formulations have a value of about 22–30.

In the two phase formulations of the invention, "L" can be set at a desired value in order to calculate the required ratios of the ingredients.

Preferred film-forming compounds include $C_{16-20}$ saturated alkanols such as hexadecan-1-ol and $C_{16-18}$ saturated amines. Preferred emulsifiers and solvents for the first phase are as described hereinbefore for European Patent Specification 331474, which is incorporated herein by reference.

The use of the two phase formulations of the invention will be dependent upon the nature of the active ingredients included within the formulation but the formulations will commonly be used to control pesticidal infestations such as insect, acarine or helminth or microbial infestations. The application rate of the active ingredients will correspond to the application rates of these actives when applied conventionally for that particular use.

A preferred formulation of the present invention contains 20% of chloropyrifos methyl and 1% of deltamethrin, cetyl alcohol being the stabilizer. This formulation is useful for the treatment of stored crops such as grain, in particular, against insect pests, of the orders Coleoptera (e.g. Anobium, Ceutorhynchus, Rhynchophorus, Cosmopolites, Lissorhoptrus, Meligethes, Hypothenemus, Hylesinus, Acalymma, Lema, Psylliodes, Leptinotarsa, Gonocephalum, Agriotes, Dermolepida, Heteronychus, Phaedon, Tribolium, Sitophilus, Oryzaephilus, Rhyzopertha, Prostephanus, Cryptoletes, Trogoderma, Typheae, Diabrotica, Anthonomus or Anthrenus spp.), Lepidoptera (e.g. Ephestia, Mamestra, Earias, Pectinophora, Ostrinia, Trichoplusia, Pieris, Plodia, Sitotroga, Corcyra, Laphygma, Agrotis, Amathes, Wiseana, Tryporysa, Diatrae, Sporganothis, Cydia, Archips, Plutella, Chilo, Heliothis, Spodoptera or Tineola spp.), Diptera (e.g. Musca, Aedes, Anopheles, Culex, Glossina, Simulium, Stomoxys, Haematobia, Tabanus, Hydrotaea, Lucilia, Chrysomla, Callitroga, Dermatobia, Gasterophilus, Hypoderma, Hylemyia, Atherigona, Chlorops, Phytomyza, Ceratitis, Liriomyza and Melopbagus spp.), Phthiraptera (Malophaga e.g. Damalina spp. and Anoplura e.g. Linognathus and Haematopinus spp.), Hemiptera (e.g. Aphis, Bemisia, Photodon, Aeneolamia, Empoasca, Parkinsiella, Pyrilla, Aonidiella, coccus, Pseudococus, Helopeltis, Lygus, Dysdercus, Oxycarenus, Nezara, Aleurodes, Triatoma, Psylla, Mysus, Megourn, Pbylloxera, Adelyes, Niloparvata, Nephrotetix or Cimex spp.), Orthoptera (e.g. Locusta, Gryllus, Schistocerca or Acheta spp.), Dictyoptera (e.g. Blattella, Periplaneta or Blatta spp.) Hymenoptera (e.g. Athalia, Cephus, Atta, Solenopsls or Monomorium spp.), Isoptera (e.g. Odontotermes and Reticulitermes spp.), Siphonaptera (e.g. Ctencephalides or Pulex spp.), Thysanura (e.g. Lepisma spp.), Dermaptera (e.g. Forficula spp.), Pscoptera (e.g. Peripsocus spp.) and Thysanoptera (e.g. *Thrips tabaci*),. Acarine pests include ticks, e.g. members of the genera Boophilus, Ornithodorus, Rhipicephalus, Amblyomma, Hyalomma, Ixodes, Haemaphysalis, Dermacentor and Anocentor, and mites and manges such as Acarus, Tyrophagus, Glycyphagus, Tetranychus, Psoroptes, Notoednes, Sarcoptes, Psorergates, Chorioptes, Eutrombicula, Demodex, Panonycbus, Bryobia, Eriophyes, Blaniulus, Polyphagotarsonemus, Scutigerella, and Oniscus spp. and Periplaneta, Blatta, Blattella and Lapisma.

The two phase formulations may be prepared as follows:

1) The first active is dissolved in a solvent to form, or is itself, the first phase.
2) The stabilizer is dissolved into the first phase.
3) The second active ingredient is dispersed in part of the second phase.

4) The surfactants are dispersed either into the first phase or into the part of the second phase containing the second active ingredient.
5) The first phase is then dispersed into that part of the second phase that does not contain the second active ingredient.
6) The remainder of the second phase containing the second active ingredient is mixed with the mixture of the first phase and the other part of the second phase. Step (6) is not carried out under high sheer conditions. Therefore the second portion of the second phase simply combines with the first portion of the second phase and the end result is a first-phase-in-second-phase dispersion or emulsion.

In the following examples, there are described several preferred embodiments to illustrate the invention. However, it should be understood that the invention is not intended to be limited to the specific embodiments.

EXAMPLE 1A

A ULV insecticide formulation was made up of the following components.

|  | % mass/mass | Rel. molar mass |
|---|---|---|
| Oil phase |  |  |
| Permethrin | 10.32 | 391 |
| S-Bioallethrin | 1.51 | 302 |
| Piperonyl Butoxide | 11.32 | 338 |
| Odorless kerosene | 9.30 | 170 |
| Hexadecan-1-ol | 3.00 | 242 |
| Emulsifiers |  |  |
| Tegoplant EM11 | 0.75 |  |
| Brij 76 | 0.24 |  |
| Tween 20 | 0.01 |  |
| Aqueous phase |  |  |
| Water | 63.45 | 18 |
| Silcolapse 5000 | 0.10 |  |
| "Silcolapse" is a Regd. T.M. |  |  |

The concentrate was diluted in 1+9 parts with water for application. The average relative molar mass of oil phase= 271 and the molar solubility ratio (moles oil phase/moles alkanol)=9.4.

Model prediction: ratio (mass oil phase/mass of alkanol) of a formulation within the scope of the invention:

Maximum ratio with an evaporation rate (L) of 15=27.5 with L of 10=17 and with L of 5=7. Hence, the invention encompasses all such formulations where the mass ratio for this solvent/pesticide mixture to hexadecan-1-ol is less than or equal to 27.

The above formulation has the ratio (mass of oil phase/mass of alkanol)=10.8 and the ratio (moles water/moles of alkanol)=4318 when diluted. Observed average evaporation rate (L)=3.8.

EXAMPLE 1B

A ULV insecticide spray

| | % mass/mass | Rel. molar mass |
|---|---|---|
| Oil phase | | |
| Permethrin | 10.87 | 391 |
| S-Bioallethrin | 0.15 | 302 |
| Piperonyl Butoxide | 11.07 | 338 |
| Odorless kerosene | 9.30 | 170 |
| Hexadecan-1-ol | 3.00 | 242 |
| Emulsifiers | | |
| Tegoplant EM11 | 0.75 | |
| Brij 76 | 0.24 | |
| Tween 20 | 0.01 | |
| Aqueous phase | | |
| Water | 64.51 | 18 |
| Silcolapse 5000 | 0.10 | |
| "Silcolapse" is a Regd. T.M. | | |

EXAMPLE 2A

A ULV insecticide formulation

| | % mass/mass | Rel. molar mass |
|---|---|---|
| Oil phase | | |
| Delamethrin | 1.0 | 505 |
| Heptyl acetate (Exxate 700) [Exxon Chemicals] | 30.0 | 158 |
| Hexadecan-1-ol | 5.0 | 242 |
| Emulsifier | | |
| Tegoplant EM11 | 1.0 | 800 |
| Aqueous phase | | |
| Silcolapse 5000 (anti foam agent) | 0.1 | — |
| Water | 62.9 | 18 |

The concentrate was diluted in 1+19 parts with water for spray application and the parameters for these and the subsequent Examples are given in Table 1.

EXAMPLE 3

A ULV insecticide formulation

| | % mass/mass | Rel. molar mass |
|---|---|---|
| Oil phase | | |
| Alpha cypermethrin | 2.0 | 416 |
| Heptyl acetate (Exxate 700) [Exxon Chemicals] | 30.0 | 158 |
| Hexadecan-1-ol | 7.0 | 242 |
| Emulsifier | | |
| Tegoplant EM11 | 0.1 | 800 |
| Aqueous phase | | |
| Water | 60.0 | 18 |
| Observed average evaporation rate = 4.5 | | |

EXAMPLE 4

A ULV insecticide formulation

| | % mass/mass | Rel. molar mass |
|---|---|---|
| Oil phase | | |
| Permethrin | 25.0 | 391 |
| 4-methylpentan-2-one | 32.0 | 100 |
| Hexadecan-1-ol | 6.0 | 242 |

-continued

|  | % mass/mass | Rel. molar mass |
|---|---|---|
| Propan-2-ol | 32.0 | —* |
| Emulsifiers |  |  |
| Tween 80 | 3.6 |  |
| Span 80 | 1.4 |  |

* assumed to partition mostly into the aqueous phase on dilution as it was water-miscible. This formulation was found to be particularly effective.

EXAMPLE 4B

A ULV insecticide spray

|  | % mass/mass | Rel. molar mass |
|---|---|---|
| Oil phase |  |  |
| Permethrin | 25.0 | 391 |
| Hexadecan-1-ol | 6.0 | 242 |
| Emulsifiers |  |  |
| PMO | 3.6 |  |
| SMO | 1.4 |  |
| Aqueous phase | none |  |

EXAMPLE 5

A pressure packed insecticide formulation

|  | % mass/mass | Rel. molar mass |
|---|---|---|
| Oil phase |  |  |
| Bioallethrin | 0.315 | 302 |
| Permethrin | 0.038 | 391 |
| Odorless kerosene | 8.3 | 170 |
| Butane | 40.0 | —* |
| Hexadecan-1-ol | 1.0 | 242 |
| Emulsifier |  |  |
| Tegoplant EM11 | 1.0 | 800 |
| Aqueous phase |  |  |
| Water | 50.347 | 18 |

* excluded due to its volatility (vapor at normal temperatures and pressures)

EXAMPLE 6

A ULV insecticide formulation

|  | % mass/mass | Rel. molar mass |
|---|---|---|
| Oil phase |  |  |
| Pyrethrins (PY) | 2.0 | 350 |
| Solvent in PY extract | 6.0 | 150 |
| Piperonyl Butoxide | 16.0 | 338 |
| Octadecan-1-ol | 2.5 | 270 |
| Emulsifier |  |  |
| Tegoplant EM11 | 1.0 | 800 |
| Aqueous phase |  |  |
| Water | 72.4 | 18 |
| Silcolapse 5000 | 0.1 | — |

Ready use concentrate (no further dilution required).

EXAMPLE 7

A ULV insecticide formulation

|  | % mass/mass | Rel. molar mass |
|---|---|---|
| Oil phase |  |  |
| Chlorpyrifos-methyl | 20.0 | 323.0 |
| Solvesso 150 | 20.0 | 144.0 |
| [Exxon Chemicals] |  |  |
| Hexadecan-1-ol | 3.0 | 242 |
| Emulsifier |  |  |
| Tegoplant EM11 | 2.0 | — |
| Aqueous phase |  |  |
| Water | 54.9 | 18 |
| Silcolapse 5000 | 0.1 | — |

EXAMPLE 8

A wettable powder formulation

|  | % mass/mass | Rel. molar mass |
|---|---|---|
| Inorganic carrier |  |  |
| Celite 204 | 64.0 | — |
| Oil phase |  |  |
| Permethrin | 25.0 | 391 |
| Hexadecan-1-ol | 6.0 | 141 |
| Emulsifiers/dispersing agents |  |  |
| Tegoplant EM11 | 1.0 |  |
| Sodium diisopropyl naphthalene sulfonate e.g. Aerosol OS [Cyanamid G.B. Ltd.] | 4.0 |  |

EXAMPLE 9

A ULV herbicide formulation (containing a water soluble herbicide).

|  | % mass/mass | Rel. molar mass |
|---|---|---|
| Oil phase |  |  |
| Solvesso 200 | 10.0 | 163.0 |
| Hexadecan-1-ol | 3.0 | 242 |
| Emulsifiers |  |  |
| Span 80 | 6.6 |  |
| Tween 80 | 3.4 |  |
| Aqueous phase |  |  |
| Water | 40.0 | 18 |
| Glyphosate-mono isopropylammonium | 36.9 |  |

This formulation may be modified for other water-miscible active ingredients, for example the components of Bordeaux mixture or quaternary ammonium compounds.

EXAMPLE 10

An LV synergist spray

| | % mass/mass | Rel. molar mass |
|---|---|---|
| Oil phase | | |
| Piperonyl butoxide | 64.0 | 338 |
| Hexadecan-1-ol | 7.5 | 242 |
| Emulsifiers | | |
| NPE 80 | | 7.0 |
| Aqueous phase | none | |
| Inert/Water Soluble ingredients | | |
| Propan-2-ol | 21.5 | |

EXAMPLE 11

An LV insecticide spray

| | % mass/mass | Rel. molar mass |
|---|---|---|
| Oil phase | | |
| Solvesso 150 | 8.8 | 144 |
| Hexadecan-1-ol | 1.2 | 242 |
| Emulsifiers | | |
| SMO | | 0.3 |
| PMO | | 0.9 |
| Aqueous phase | none | |
| Inert/Water Soluble ingredients | | |
| Dimethoate | 80.0 | |
| Propan-2-ol | 8.8 | |

EXAMPLE 12

A wettable powder insecticide spray

| | % mass/mass | Rel. molar mass |
|---|---|---|
| Oil phase | | |
| Solvesso 150 | 25.0 | 144 |
| Hexadecan-1-ol | 5.0 | 242 |
| Emulsifiers | | |
| SDNS | | 7.5 |
| Aqueous phase | none | |
| Inert/Water Soluble ingredients | | |
| Diflubenzuron | 25.0 | |
| Mineral silicates | 37.5 | |

EXAMPLE 13

A flowable fungicide spray

| | % mass/mass | Rel. molar mass |
|---|---|---|
| Oil phase | | |
| Solvesso 150 | 15.0 | 144 |
| Hexadecan-1-ol | 6.0 | 242 |
| Emulsifiers | | |
| SMO | | 1.4 |
| PMO | | 3.6 |
| Aqueous phase | | |

-continued

| | % mass/mass | Rel. molar mass |
|---|---|---|
| Water (pH = 13) | 48.9 | 18 |
| Sodium hydroxide | 0.1 | |
| 1,2 propandiol | 4.0 | |
| Inert/Water Soluble ingredients | | |
| Thiabendazole | 20.0 | |
| Xanthan gum | 0.5 | |
| Mineral silicates | 0.5 | |

EXAMPLE 14

An LV insecticide spray

| | % mass/mass | Rel. molar mass |
|---|---|---|
| Oil phase | | |
| Exxate 700 | 5.0 | 158 |
| Hexadecan-1-ol | 4.0 | 242 |
| Emulsifiers | | |
| OE/PGO | 2.4 | |
| Aqueous phase | none | |

EXAMPLE 15

A ULV insecticide spray

| | % mass/mass | Rel. molar mass |
|---|---|---|
| Oil phase | | |
| Cypermethrin | 10.0 | 416 |
| Solvesso 150 | 40.0 | 144 |
| Hexadecan-1-ol | 4.0 | 242 |
| Emulsifiers | | |
| OE/PGO | 2.0 | |
| Aqueous phase | | |
| Water | 44.0 | |
| Inert/Water Soluble ingredients | none | |

EXAMPLE 16

A ULV insecticide spray

| | % mass/mass | Rel. molar mass |
|---|---|---|
| Oil phase | | |
| Methoprene | 28.0 | 311 |
| Solvesso 150 | 28.0 | 144 |
| Hexadecan-1-ol | 7.0 | 242 |
| Emulsifiers | | |
| NPE | | 4.0 |
| Aqueous phase | none | |
| Inert/Water Soluble ingredients | | |
| Propan-2-ol | 33.0 | |

EXAMPLE 17

An LV insecticide spray

|  | % mass/mass | Rel. molar mass |
|---|---|---|
| Oil phase |  |  |
| Amitraz | 18.0 | 293 |
| Solvesso 150 | 36.0 | 144 |
| 1-Hexadecylamine | 16.3 | 242 |
| Emulsifiers |  |  |
| SMO |  | 1.8 |
| PMO |  | 4.5 |
| Aqueous phase | none |  |
| Inert/Water Soluble ingredients |  |  |
| Propan-2-ol | 23.4 |  |

EXAMPLE 18

An LV insecticide spray

|  | % mass/mass | Rel. molar mass |
|---|---|---|
| Oil phase |  |  |
| Malathion | 65.0 | 330 |
| Hexadecan-1-ol | 7.5 | 242 |
| Emulsifiers |  |  |
| SMO |  | 2.0 |
| PMO |  | 5.0 |
| Aqueous phase | none |  |
| Inert/Water Soluble ingredients |  |  |
| Propan-2-ol | 20.5 |  |

EXAMPLE 19

An LV insecticide spray

|  | % mass/mass | Rel. molar mass |
|---|---|---|
| Oil phase |  |  |
| Fenitrothion | 65.0 | 277 |
| Hexadecan-1-ol | 4.0 | 242 |
| Emulsifiers |  |  |
| SMO |  | 2.0 |
| PMO |  | 5.0 |
| Aqueous phase | none |  |
| Inert/Water Soluble ingredients |  |  |
| Propan-2-ol | 24.0 |  |

COMPARATIVE EXAMPLE A (A ULV INSECTICIDE FORMULATION).

| Oil phase | % mass/mass | Rel. molar mass |
|---|---|---|
| Permethrin | 10.8 | 391 |
| S-Bioallethrin | 1.7 | 302 |
| Piperonyl Butoxide | 12.3 | 338 |
| Mineral Oil | 20.0 | 296 |
| Kerosene | 41.7 | 170 |
| Hexadecan-1-ol | 1.0 | 242 |
| Nonylphenol ethylene oxide condensate** | 8.2 | 638 |
| Calcium dodecyl benzenesulfonate** | 4.3 | 394 |

**emulsifiers assumed to partition mostly into aqueous phase on dilution.

Diluted 1+9 with water for application and the average relative molar mass of oil phase=254. The molar solubility ratio (moles oil phase/moles long chain alcohol)=10.0.

Model prediction ratio (mass of oil phase/mass of alkanol) of a formulation within the scope of the invention:

Maximum ratio with an evaporation rate (L) of 15 units=33.0, with an L of 10 units=20.4, and with an L of 5 units=9.0. The above formulation had the ratio (moles of oil phase/moles long chain alcohol)=86, and was therefore outside the scope of the invention. The ratio (moles of water/moles of alkanol)=12100 on dilution. Observed average evaporation rate=20 units

* Example 1 of GB-A-2 095 109.

ANALYSIS OF FORMULATIONS

The analysis of a given formulation to determine whether it satisfies the formula above is illustrated as follows:

Analysis of Example 1A:

The permethrin, S-bioallethrin, piperonyl butoxide, odorless kerosene, emulsifiers and antifoam agent constitute the oil phase and each one of these components may be taken in turn at the level in the formulation and diluted in water (%1+9). One could observe that the permethrin, S-bioallethrin, odorless kerosene and piperonyl butoxide were not miscible with water at this dilution level, e.g. permethrin has a solubility of 0.2 mg/l of water at 30° C. These components therefore constitute the oil phase. The emulsifiers would be miscible with water giving a clear solution upon dilution. Of the antifoam agent, (0.1%) 30% of this would not be soluble in the oil phase or the water and would simply be classed as an inert ingredient. The oil phase would then be constituted in the proportions in the formulation. The solubility limit of hexadecan-1-ol was determined by preparing a series of mixtures and noting the maximum composition at which all the hexadecan-1-ol remained in solution at 27° C. after a period of 24 hours. A mixture containing 8.7% mass/mass of hexadecan-1-ol was the composition in this case. The relative molar mass of the oil phase was also required and this was calculated as follows from the relative molar mass of each component and the proportions in the oil phase:

$$\frac{10.32}{391} + \frac{1.51}{302} + \frac{11.32}{338} + \frac{9.30}{170} = \frac{32.45}{RMM \text{ mixture}}$$

$$RMM \text{ mixture} = 271$$

The relative molar mass of hexadecan-1-ol was 242. The molar solubility ratio (moles oil phase/moles film forming agent)

$$=((100-8.7)/271)/(8.7/242)=9.37$$

This provided all the variables to use in the right hand side of the equation. With L=15, the predicted maximum ratio of mass oil phase of film forming agent was 27. The above formulation had a mass oil phase to film forming agent of 10.8 (33.45/3). Therefore, it was clearly within the scope of the formula. The level of hexadecan-1-ol could be reduced to 1.21% with the same level of oil phase and still remained with the scope of the formula. However, a formulation with 1.0% hexadecan-1-ol would be outside the scope of the formula.

Analysis of Example 4A:

This formulation contained permethrin, 4-methylpentan-2-one, hexadecan-1-ol, emulsifiers and propan-2-ol and the formulation was diluted 1+9 parts with water for use.

All the components given could potentially constitute the oil phase, once diluted. Propan-2-ol was completely miscible with water over all compositions and the emulsifiers were also water miscible when diluted. The permethrin and 4-methyl pentan-2-one were not completely miscible with water when diluted at this level and the oil phase therefore consisted of permethrin and 4-methyl-pentan- 2-one. The solubility of hexadecan-1-ol was determined in this mixture as described above at 27° C. The solubility of hexadecan-1-ol in the mixture of permethrin and 4-methylpentan-2-one was 16.0% mass/mass and the relative molar mass of the oil phase was calculated from the relative molar mass of the components and their proportion in the oil phase:

$$\frac{25.0}{391} + \frac{32.0}{100} = \frac{87.0}{RMM \text{ mixture}}$$

RMM mixture = 149

The relative molar mass of hexadecan-1-ol was 242 and the molar solubility ratio (moles oil phase/moles film forming agent)

$$=([100-16.11]/149)/(16/242)=8.5$$

This gave all the variables to be used on the right hand side of the formula. With L=15, then the maximum ratio of oil phase to hexadecan-1-ol was 66. The above formulation had a mass ratio of oil phase to film-forming agent of 9.5 and was well within the scope of the formula. The level of hexadecan-1-ol could be reduced to 0.87% while maintaining the oil phase levels constant and still remained within the scope of the formula.

Analysis of Example 4B:

It will be observed that this formulation was the same as that given as Example 4A except that the formulation was diluted 1+29 parts with water. Permethrin was the only component within the formulation that was immiscible with water at this level of dilution. 0.32 g of 4-methyl-pentan-2-one dissolved completely in 29 g of water and the permethrin in this example constituted the oil phase. The solubility of hexadecan-1-ol in permethrin was 1.8% w/w which gave a molar solubility ratio of 33.7.

With L=15, the maximum ratio of oil phase to film-forming agent was 99. At this dilution level, the level of hexadecan-1-ol in the formulation could be reduced to 0.4% and still remained within the scope of the formula. This also provided an example of where the evaporation rate of a formulation was improved as a result of further dilution because of additional partitioning of one of the oil phase components in the aqueous phase. There was less oil phase for the film forming agent to dissolve in, thus more was available to form a film at the surface of the droplet.

Analysis of Example 13:

This formulation contained Solvesso 150, hexadecan-1-ol, emulsifiers, water, sodium hydroxide, 1,2-propandiol, thiabendazole, xanthan gum, and mineral silicates which was a fairly complex formulation. The active ingredient was not particularly soluble in the aqueous or oil phase and a fine particulate suspension of the active ingredient was therefore made. The formulation also contained a thickening agent to aid the suspension of the particulates. This was a high molecular weight polysaccharide that was insoluble in the oil phase and it can be regarded as an inert substance. The formulation also contained powered mineral silicates of low bulk density to prevent the formulation from "caking" (particles sticking together). The 1,2-propandiol was added to prevent freezing and was completely water miscible. The sodium hydroxide was added to buffer the formulation at around a pH of 13 and was water soluble. The oil phase consisted of only Solvesso 150 with possibly a small amount of thiabendazole dissolved in it.

The solubility of hexadecan-1-ol in Solvesso 150 was 23.5% mass/mass and the relative molar mass of Solvesso 150 was 144. The molar solubility was 5.5. The right hand side of the formula with L=15, gave a ratio (mass of oil phase/mass of film forming agent)=35. The formulation had a mass ratio of 2.5 and was clearly within the scope of the formula. The level of hexadecan-1-ol could be reduced substantially and the formulation remained within the scope of the formula.

TABLE 1

| Example No: | 1A | 1B | 2 | 3 | 4A | 4B | 5 |
| --- | --- | --- | --- | --- | --- | --- | --- |
| Dilution for appln. 1 + n | 9 | 9 | 19 | 29 | 9 | 29 | 0 |
| Av. Rel. Molar mass of oil phase | 271 | 271 | 162 | 164 | 149 | 391 | 173 |
| Mass solubility | 8.7 | 8.7 | 16.5 | 16.5 | 16.0 | 1.8 | 7.5 |
| Molar solubility ratio | 9.4 | 9.4 | 7.6 | 7.5 | 8.5 | 33.7 | 17.2 |
| Maximum ratio | | | | | | | |

TABLE 1-continued

| calcd. for L | | | | | | | |
|---|---|---|---|---|---|---|---|
| L = 15 | 27 | 27 | 47 | 45 | 66 | 99 | 145 |
| L = 10 | 17 | 17 | 29 | 28 | 41 | 61 | 90 |
| L = 5 | 7 | 7 | 13 | 12 | 18 | 27 | 40 |
| Mass of oil Mass of film-former | 10.8 | 10.5 | 6.2 | 4.6 | 9.5 | 9.5 | 8.6 |
| L measured | 3.8 | 3.8 | 4.0 | 4.5 | 5.0 | 4.2 | 3.8 |
| Moles (water) Moles (film-former) | 4318 | 5278 | 5278 | 5685 | 2016 | 6498 | 663 |

| Example No. | 6 | 7 | 8 | 9 | 10 | 11 | 12 |
|---|---|---|---|---|---|---|---|
| Dilution for appln. 1 + n | 0 | 14 | 39 | 39 | 39 | 29 | 39 |
| Av. Rel. Molar mass of oil phase | 258 | 199 | 391 | 153 | 338 | 144 | 144 |
| Mass solubility | 4.0 | 9.0 | 1.8 | 12.5 | 5.5 | 23.5 | 23.5 |
| Molar solubility ratio | 25.1 | 12.2 | 33.7 | 10.4 | 12.3 | 5.5 | 5.5 |
| Maximum ratio calcd. for L | | | | | | | |
| L = 15 | 116 | 68 | 99 | 75 | 28 | 35 | 35 |
| L = 10 | 72 | 42 | 61 | 47 | 17 | 22 | 22 |
| L = 5 | 32 | 19 | 99 | 21 | 8 | 10 | 10 |
| Mass of oil Mass of film-former | 2.5 | 9.6 | 13.3 | 8.5 | 8.5 | 5.0 | 5.0 |
| L measured | 4.8 | 4.7 | 5.3 | 3.8 | 5.3 | 7.5 | 7.0 |
| Moles (water) Moles (film-former) | 435 | 6520 | 6691 | 32490 | 6991 | 11089 | 10487 |

| Example No. | 13 | 14 | 15 | 16 | 17 | 18 | 19 |
|---|---|---|---|---|---|---|---|
| Dilution for appln. 1 + n | 49 | 19 | 19 | 19 | 19 | 19 | 19 |
| Av. Rel. Molar mass of oil phase | 144 | 158 | 166 | 197 | 173 | 330 | 277 |
| Mass solubility | 23.5 | 16.5 | 15.0 | 18.5 | 20.1 | 1.9 | 0.8 |
| Molar solubility ratio | 5.5 | 7.8 | 8.2 | 5.4 | 5.5 | 37.8 | 108 |
| Maximum ratio calcd. for L | | | | | | | |
| L = 15 | 35 | 51 | 52 | 20 | 26 | 157 | 1038 |
| L = 10 | 22 | 32 | 32 | 13 | 16 | 97 | 643 |
| L = 5 | 10 | 14 | 14 | 6 | 7 | 43 | 284 |
| Mass of oil Mass of film-former | 2.5 | 1.3 | 12.5 | 8.0 | 3.3 | 8.7 | 16.3 |
| L measured | 7.5 | 7.3 | 4.7 | 7.8 | 4.5 | 6.4 | 5.1 |
| Moles (water) Moles (film-former) | 11089 | 9747 | 6534 | 3649 | 1567 | 3402 | 6386 |

EXAMPLE 20

Formulations

| Ingredients | % w/w |
|---|---|
| chlorpyrifos methyl | 19.15 |
| solvesso 150 | 19.15 |
| water (deionised) | 51.40 |
| emulsifiers | 2.00 |
| Deltamethrin (20% SC) | 5.20 |

The deltamethrin (20% SC) contained deltamethrin (20%) in water with surfactant, thickening agents and biological preservative. The oil phase was prepared by dissolving cetyl alcohol in a solution of chlorpyrifos methyl in Solvesso 150 at a temperature up to 50° C. The emulsifiers were added to the water at 60° C. and the resultant aqueous solution was cooled to 50° C. (aqueous phase). The oil phase was added to the aqueous phase at 50° C. with vigorous mixing and the resultant emulsion was cooled to 20° C. A 20% aqueous suspension of deltamethrin was added with stirring at 20°–25° C.

EXAMPLE 21

Stability Testing

Tests were carried out on the stability of active ingredients in a formulation of the present invention (A) and in a two phase formulation that did not contain stabilizer (B).

Formulation A Results

A chlorpyrifos methyl/deltamethrin formulation with film-forming agent was prepared in a similar manner to Example 20 above.

Typical Stability Data: chlorpyrifos methyl (CPMe) tests (figures±10%)

| Time in months (M) | 25° C. | 38° C. | 50° C. |
|---|---|---|---|
| Initial | 100 | 100 | 100 |
| 3 M or 4 M | 101 | 103 | 103 |

| | | | |
|---|---|---|---|
| 6 M | 102 | 100 | 103 |
| 12 M | 101 | 94 | 101 |

Typical Stability Data: Deltamethrin (DLTM)

| Time in months (M) | 25° C. | 38° C. | 50° C. |
|---|---|---|---|
| Initial | 100 | 100 | 100 |
| 3 M or 4 M | 96 | 99 | 98 |
| 6 M | 97 | 103 | 103 |
| 12 M | 98 | 94 | 76 |

Formulations B—results

A chlorpyrifos methyl/Deltamethrin Formulation without film forming agent.

Typical Stability Data: CPME

| Time in months (M) | 25° C. | 38° C. | 50° C. |
|---|---|---|---|
| Initial | 100 | 100 | 100 |
| 3 M | 112 | 106 | 71 |

Typical Stability Data: DLTM

| Time in months (M) | 25° C. | 38° C. | 50° C. |
|---|---|---|---|
| Initial | 100 | 100 | 100 |
| 3 M | 75 | 75 | 16 |

The results show formulations (B) without film forming agent are relatively unstable.

EXAMPLE 22

Biological Testing

Protocol: An appropriately water-diluted formulation was sprayed on to 400 tons of grain at Wail, Victoria. It was applied to the grain stream during turning at one liter of spray per ton. Treated grain was sampled at intervals by a vacuum probe and bioassays were conducted by holding 100 adult insects on 150 g or 300 g of grain. After 3 weeks of incubation at 25° C. and 55–60% relative humidity, the insects were sieved off and mortality counted. The grain was further sieved at 7, 9, and 11 weeks to remove and mortality count adult progeny.

(1) 0.24; 4.9 mg/kg deltamethrin; chlorpyrifos-methyl

| Insects tested | Months of post-treatment storage | % Mortality | Progeny numbers living | Progeny numbers dead | Progeny suppression % |
|---|---|---|---|---|---|
| Sitophilus | 0 | 100 | 0 | 4 | 99.8 |
| oryzae | 1.5 | 100 | 0 | 0 | 100 |
| | 3 | 100 | 0 | 0 | 100 |
| | 4.5 | 100 | 0 | 0 | 100 |
| | 6 | 100 | 0 | 0 | 100 |
| | 9 | 100 | 0 | 0 | 100 |
| Rhyzopertha | 0 | 100 | 0 | 0 | 100 |
| dominica | 1.5 | 100 | 0 | 0 | 100 |
| | 3 | 100 | 0 | 0 | 100 |
| | 4.5 | 100 | 0 | 0 | 100 |
| | 6 | 100 | 0 | 0 | 100 |
| | 9 | 100 | 0 | 0 | 100 |
| Tribolium | 0 | 100 | 0 | 0 | 100 |
| castaneum | 1.5 | 100 | 0 | 1 | 99.7 |
| | 3 | 100 | 0 | 0 | 100 |
| | 4.5 | 100 | 0 | 1 | 99.5 |
| | 6 | 100 | 0 | 4 | 99.0 |
| | 9 | 100 | 0 | 0 | 100 |
| Queensland | 0 | 100 | 0 | 0 | 100 |
| Tribolium | 1.5 | 100 | 0 | 2 | 97 |
| castaneum | 3 | 99 | 0 | 0 | 100 |
| | 4.5 | 99 | 0 | 1 | 99.7 |
| | 6 | 100 | 0 | 4 | 99.0 |
| | 9 | 95 | 0 | 0 | 100 |

Results show good control of insect pests for post-treatment storage up to 9 months.

Various modifications of the compositions and method of the invention may be made without departing from the spirit or scope thereof and it is to be understood that the invention is intended to be limited only as defined in the appended claims.

What we claim is:

1. Formulation suitable for spraying or for dilution with water to form a sprayable preparation, the formulation comprising an active ingredient, optionally a carrier or solvent for the active ingredient, an emulsifier and an evaporation retardant, characterized in that the formulation satisfies the following Formula:

$$\frac{\text{mass of oil phase}}{\text{mass of retardant}} \leq \frac{M_{oil}}{M_{retardant}} \times \text{Exp}\left[\frac{\ln\left(\frac{L}{4}\right) + C\ln(AX^B)}{C}\right]$$

where L is less than or equal to 15, A: 700376, B=−1.51, C=0.8472, $H_{oil}$ is the weighted average relative molar mass of the oil phase, $M_{retardant}$ is the weighted average relative molar mass of the retardant, and $$X = \frac{(M_{oil})^{1.8}}{Y}$$

where Y is the molar solubility ratio of the formulation, defined as the minimum number of moles of the oil phase which will dissolve the retardant, divided by the number of moles of retardant, provided that, in the Formula above, any solvent which has no liquid phase at 27° C. at atmospheric pressure is excluded.

2. A Formulation according to claim 1 wherein L is less than 10.

3. A formulation according to claim 2 wherein L is less than 5.

4. A Formulation according claim 1 wherein the active ingredient is a pesticide or herbicide.

5. A formulation according to claim 4 wherein the active ingredient is a pyrethroid.

6. A formulation according to claim 1 where in the solvent has a relative molar mass of less than 200.

7. A formulation according to claim 6 herein the solvent comprises kerosene, odorless kerosene, mineral oil, heptyl acetate, 4-methylpentan-2-one or butane.

8. A formulation according claim 1 wherein the formulation is an -ultra low volume concentrate and the proportion of the oil phase is between 8% and 30% by mass before dilution for use.

9. A formulation according to claim 1 wherein the formulation is a wettable power.

10. A formulation according to claim 1 wherein the evaporation retardant is hexadecan-1-ol or a mixture of hexadecan-1-ol and octadecan-1-ol.

11. A formulation according claim 10 which is to be diluted before use and which comprises from 1.0 to 7.5% evaporation retardant by mass.

12. A formulation according to claim 1 wherein the emulsifier is a non-ionic compound with an HLB value of 8–18, or a mixture of non-ionic compounds, the mixture having a weighted average HLB value of 8–18.

13. A formulation according to claim 1 which is diluted and ready for use and which comprises 0.0 to 3.2% oil phase by weight.

14. A formulation according to claim 13 which is diluted and ready for use and which comprises 0.25 to 1.5% oil phase by weight.

15. A method of combating insect or acarine pests or unwanted plants by spraying a formulation of claim 1, optionally diluted with water, wherein the formulation comprises an insecticide, acaricide or herbicide.

16. A pesticidal formulation comprising a two phase formulation, the first phase of which is water immiscible and comprises a first active ingredient, a stabilizer, and optionally an emulsifier or wetting or dispersing agent, and a carrier or solvent for the active ingredient; and a second phase immiscible with the first phase which is water and comprises a second active ingredient and optionally an emulsifier or wetting or dispersing agent and a carrier or solvent for the second active ingredient, wherein the first phase of the formulation satisfies the formula:

$$\frac{\text{mass of oil phase}}{\text{mass of stabiliser}} \leq \frac{M_{oil}}{M_{stabiliser}} \times \text{Exp}\left[\frac{\ln(L/4) + C\ln(AX^B)}{C}\right]$$

where L is less than or equal to 15, A=700376, B=−1.51. C= 0.8472

$M_{oil}$ is the weighted average relative molar mass of the oil phase $M_{stabilizer}$ is the average molar mass of the stabilizer, and $$X = \frac{(M_{oil})^{1.8}}{Y}$$

where Y is the molar solubility ratio of the formulation, defined as the minimum number of moles of oil phase which will dissolve the stabilizer, divided by the number of moles of stabilizer, provided that, in the formula above, any solvent which has no liquid phase at 27° C. at atmosphere pressure is excluded.

17. A pesticidal formulation according to claim 16 wherein L is less than 5.

18. A pesticidal formulation according to claim 16 wherein the stabilizer is a $C_{16-20}$ saturated alkanol, or $C_{16-18}$ saturated amine.

* * * * *